United States Patent
Koskan et al.

[11] Patent Number: 5,814,582
[45] Date of Patent: Sep. 29, 1998

[54] METHOD FOR ENHANCED PLANT PRODUCTIVITY

[75] Inventors: Larry P. Koskan, Orland Park; Abdul Rehman Y. Meah, Justice; Robert J. Ross, Elmhurst; Lai-Duien Grace Fan, Lake Zurich, all of Ill.

[73] Assignee: Donlar Corporation, Bedford Park, Ill.

[21] Appl. No.: 781,651

[22] Filed: Jan. 10, 1997

Related U.S. Application Data

[63] Continuation-in-part of Ser. No. 313,436, Sep. 27, 1994, Pat. No. 5,593,947, which is a continuation-in-part of Ser. No. 972,375, Nov. 5, 1992, Pat. No. 5,350,735.

[51] Int. Cl.$^6$ .................. A01N 37/06; A01N 37/08; A01N 37/10; A01N 37/18
[52] U.S. Cl. ............................................ 504/320
[58] Field of Search ............................... 504/320

[56] References Cited

U.S. PATENT DOCUMENTS

| | | | |
|---|---|---|---|
| 3,846,380 | 11/1974 | Fujimoto et al. | 252/352 |
| 4,799,953 | 1/1989 | Danzig et al. | 71/98 |
| 4,813,997 | 3/1989 | Kinnersley et al. | 71/66 |
| 4,839,461 | 6/1989 | Boehmke | 528/363 |
| 4,863,506 | 9/1989 | Young | 71/113 |
| 4,863,898 | 9/1989 | Ashmead et al. | 514/6 |
| 5,047,078 | 9/1991 | Gill | 71/11 |
| 5,209,768 | 5/1993 | Hughes | 504/313 |
| 5,350,735 | 9/1994 | Kinnersley et al. | 504/147 |
| 5,478,919 | 12/1995 | Koskan et al. | 528/363 |
| 5,610,267 | 3/1997 | Wood et al. | 528/363 |

OTHER PUBLICATIONS

Kinnersley et. al., Plant Growth Regulation 9:137–146 (1990).

Byrnes, Fertilizer Research 26:209–215 (1990).

*Primary Examiner*—S. Mark Clardy
*Attorney, Agent, or Firm*—Olson & Hierl, Ltd.

[57] ABSTRACT

This invention relates to enhancing plant productivity employing a method which supplies to a plant a water-soluble co-polymeric acid having a molecular size larger than about 1,600 Daltons.

32 Claims, 3 Drawing Sheets

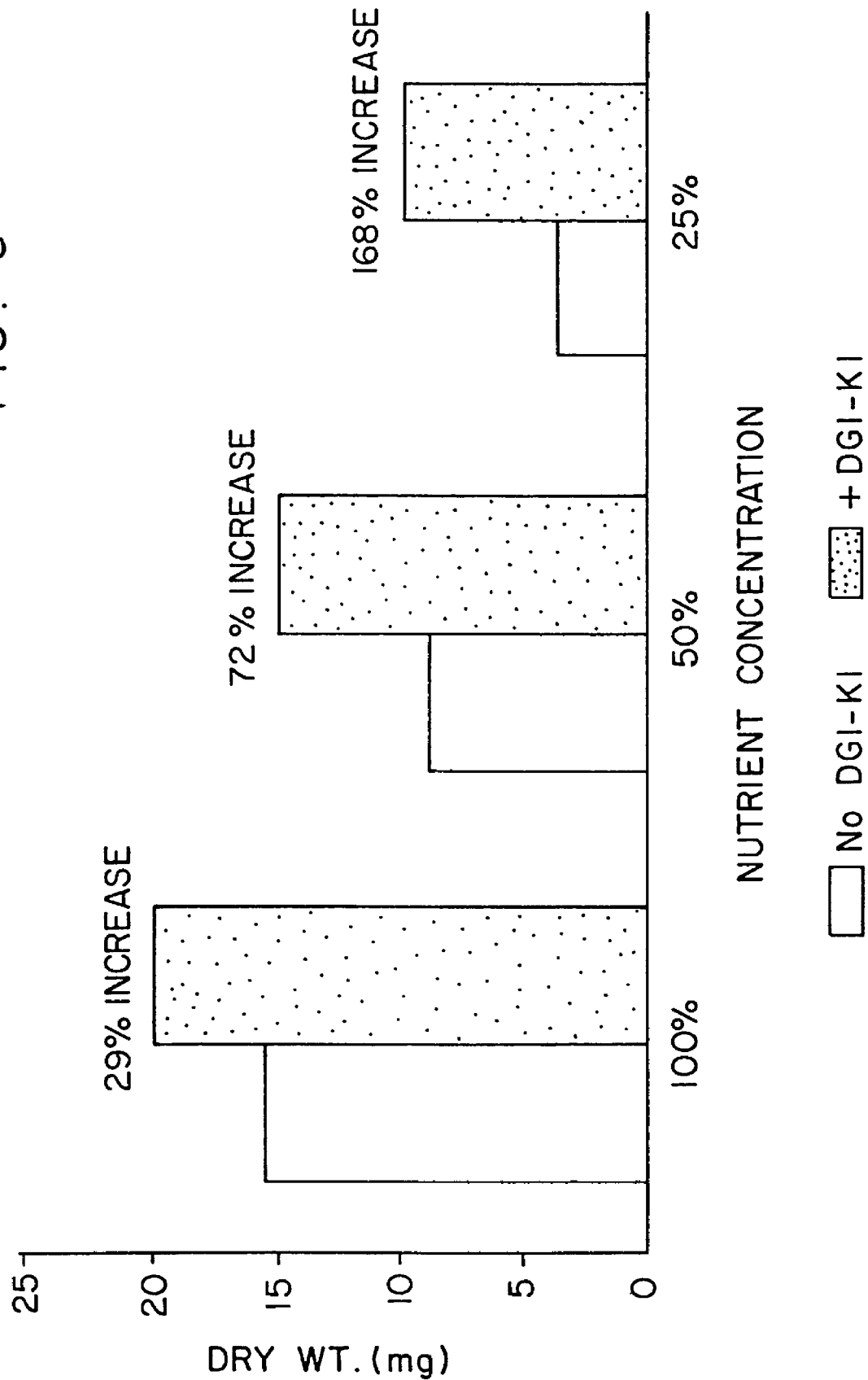

METHOD FOR ENHANCED PLANT PRODUCTIVITY

CROSS-REFERENCE TO RELATED APPLICATION

This application is a continuation-in-part of U.S. Ser. No. 08/313,436, filed on Sep. 27, 1994, now U.S. Pat. No. 5,593,947, which is a continuation-in-part of U.S. Ser. No. 07/972,375, filed on Nov. 5, 1992, now U.S. Pat. No. 5,350,735.

TECHNICAL FIELD

This invention relates to a method for enhancing the productivity of plants. More particularly, this invention relates to absorption phenomena that facilitate the utilization of nutrients by plants through either seed, root or foliar pathways.

BACKGROUND OF THE INVENTION

Organic acids and oligomers thereof have been shown to promote plant growth. Typical promoters of plant growth are described by Kinnersley et al., *Plant Growth Regulation*, 9, pp. 137–146 (1990) (lactic acid and relatively low molecular weight oligomers of lactic acid); in U.S. Pat. No. 4,813,997 to Kinnersley et al. (oligomers of glycolic and/or L-lactic acid) and in U.S. Pat. No. 4,799,953 to Danzig et al. (oligomers of thiolactic and thioglycolic acids). All of the forgoing approaches to plant growth promotion appear to focus on coordination as a means for increasing plant uptake of compounds vital to the growth of the plant, e.g., micronutrients such as calcium, magnesium, sulfur, manganese, zinc, copper, iron, boron, and the like.

A common approach to promoting plant growth has been, and continues to be, the use of nutrients (fertilizers), natural as well as synthetic. Synthetic nutrients usually provide nitrogen in a plant-usable form, such as urea for example, and/or inorganic nitrates, phosphates, or the like compounds. While such nutrients may be applied, more or less, at the convenience of the farmer, and may be applied as often as deemed desirable, the overuse of synthetic nutrients and the inefficient use of synthetic nutrients are major factors responsible for environmental problems such as eutrophication of groundwater, nitrate pollution, phosphate pollution, and the like. An overview of the undesirable effects of nitrogen fertilizer is presented by Byrnes, *Fertilizer Research*, 26, pp. 209–215 (1990).

To alleviate the problems attendant to inefficient nutrient use and nutrient overuse, there is an ongoing desire and need for environmental and production reasons to increase fertilizer efficiency and to enhance plant productivity.

The present invention addresses and ameliorates these problems by methods which provide a more favorable environment for enhancing the utilization of nutrients by germinating or growing plants resulting in enhanced plant productivity.

SUMMARY OF THE INVENTION

A method for enhancing plant productivity by achieving more efficient utilization of nutrients is provided.

The present method comprises supplying to a plant a composition containing a productivity enhancing amount of a substantially water-soluble co-polymeric acid having a molecular size larger than about 1,600 Daltons such that it is not absorbed by the plant. The amino acid content of the co-polymer is at least about 20 mole percent.

Particularly preferred for the present purposes are co-polymers of an amino acid, such as aspartic acid, and a carboxylic acid such as citric acid, adipic acid, or sulfoisophthalic acid.

The co-polymeric acids of this invention, when applied to plants, beneficially provide stress protection and promote nutrient uptake in environments containing salts present in concentrations that are normally toxic to plants. Further, a more favorable environment is provided to the plant which environment supplies the requisite nutrients at levels that are lower than usually are required with conventional fertilizers alone.

BRIEF DESCRIPTION OF THE DRAWINGS

In the drawings, there are shown photographic reproductions of corn plants treated in a particular manner alongside a control corn plant. In each case a yardstick (36 inches) is shown positioned between the photographed plants to indicate scale. In particular.

FIG. 5 is a graphical representation of growth enhancement with polyaspartic acid.

DETAILED DESCRIPTION OF PREFERRED EMBODIMENTS

Figure 1:
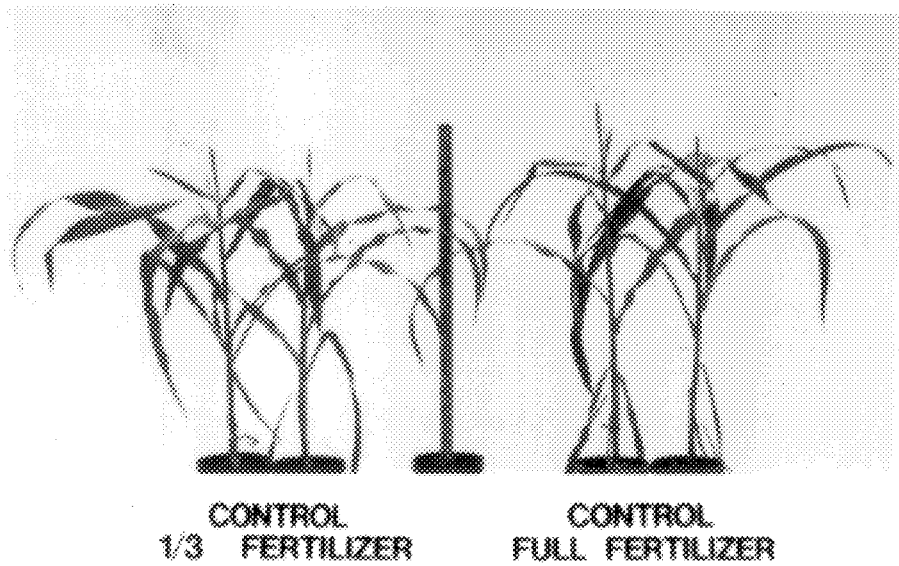
FIG. 1 shows corn plants 40 days after planting, and treated with one-third of the recommended fertilizer dosage alongside a corn plant treated with the recommended dosage for the same fertilizer.
Figure 2:
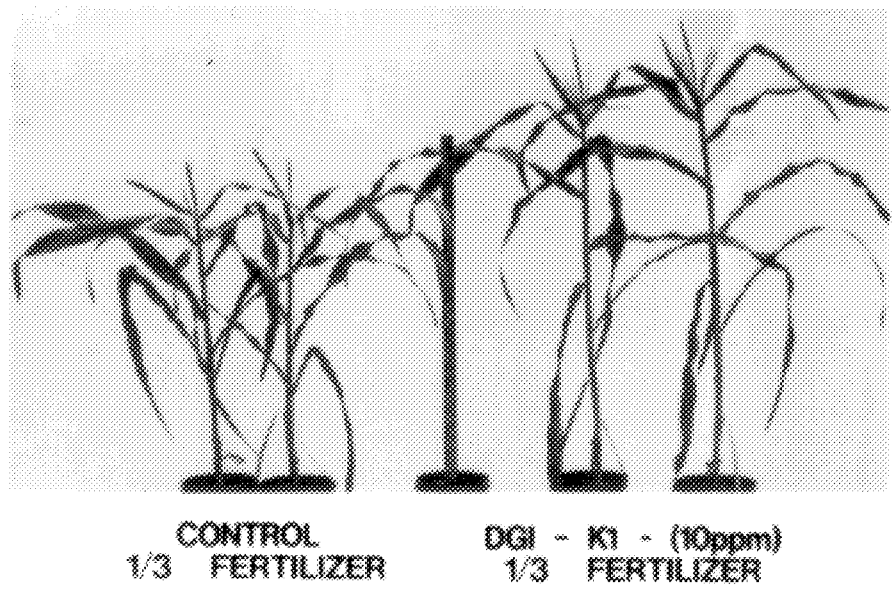
FIG. 2 shows a corn plant 40 days after planting, one treated with one third of the recommended fertilizer dosage alongside a corn plant similarly treated with the same fertilizer but also with 10 parts per million by weight of polyaspartic acid.

The present invention is predicated on the discovery that polymeric acids, and co-polymeric acids in particular, of a molecular size too large to enter a plant nevertheless provide a favorable environment for enhanced plant productivity. The more efficient utilization of nutrients can be realized in the presence of the co-polymeric acid inasmuch as relatively lower nutrient dosages can be relied upon to provide the requisite nutrients to the plant.

Enhanced plant productivity is achieved by making nutrients more readily available to the plant through its seed, root feeding zone, foliar absorption and translocation mechanisms, growth medium, or combinations of the foregoing.

The term "enhanced plant productivity" as used herein means that one or more of the following factors is achieved: increased growth rate, increased biomass, higher yields and quality (i.e., increased protein content), accelerated rate of root formation, increased tillering, increased chlorophyll concentration and the like indicia. As described herein, the term "co-polymeric acids" refers to random or block co-polymers of a carboxylic acid and an amino acid having an acidic alkyl group. The term, "carboxylic acid", as used herein, is defined as a non-peptidal compound containing a carboxyl group, —COOH.

In general, the co-polymeric acids can be supplied to the plant in the form of aqueous liquids or substantially solids in any convenient manner of application.

Preferably, aqueous nutrient solutions supplied to the plant contain at least about 10 parts per billion (ppb) by weight, preferably about 0.1 to about 1,000 parts per million (ppm) by weight, more preferably about 1 to about 500 ppm by weight of the co-polymeric acid. Such solutions can be applied to the soil surrounding the plant so as to contact the plant's root system, can be applied to the plant's foliage, seeds, or reproductive parts, can be introduced into hydroponic gardening or farming systems, or made available to the plant in any other convenient manner, in an amount as is discussed in greater detail below.

Aqueous solutions containing the co-polymeric acid also enhance plant productivity under stressful growth limiting conditions, e.g., in a growth medium that contains salts or metal ions in concentrations normally toxic to plants or in growth medium depleted in certain nutrients.

The co-polymeric acids can also be applied to soil in substantially solid form, alone or in combination with nutrients. For example, granular, pelletized, dust or powdered forms of the co-polymeric acids can be applied by gravity or air blast equipment into the furrow, row or site at seeding or planting time. Dry granular or pelleted forms of the co-polymeric acids can be impregnated or pre-formed as carriers of nutrients and can then be used for surface application by ground rig or aircraft.

The co-polymeric acids, to be suitable for the practice of the present invention, must be substantially water-soluble, and have a molecular size sufficiently large to preclude absorption into the plant. To that end, the co-polymeric acids suitable for the present purposes, while hydrophilic, have a number average molecular weight (Mw) larger than about 1,600 Daltons.

Co-polymeric acids having a molecular size in excess of about 100,000 Daltons usually do not exhibit adequate solubility in water for the present purposes. Thus a co-polymeric acid of a molecular size not larger than about 100,000 Daltons is presently preferred. A particularly suitable molecular size is in the range of about 2,000 to about 100,000 Daltons.

The content of acidic amino acid residues of the co-polymeric acid is at least about 20 mole percent. The most preferred acidic amino acids are aspartic acid in either α form (I) or β form (II), optionally containing a cyclic imide (succinimide, III) as shown in Formula A,

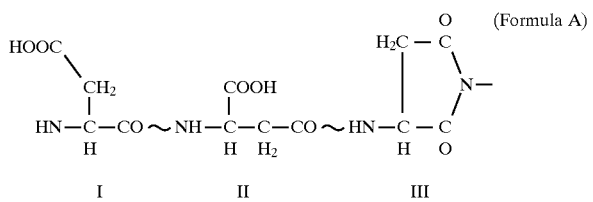

as well as glutamic acid in its α or γ form.

Random co-polymers as described above are within the purview of the present invention as are block co-polymers composed of several repetitive of poly(carboxylic acid) units and acidic poly(amino acid) units. For example, the polymeric acid component can be a block co-polymer of aspartic acid residues and L-lactic acid residues, a random co-polymer of aspartic acid residues and glycolic acid residues, a conjugated protein constituted by glutamic acid residue chains interconnected by one or more poly (carboxylic acid) residues or a polymer of acrylic acid.

Carboxylic acids and polymers thereof are commercially available. A preferred carboxylic acid is a member of the group consisting of an aliphatic carboxylic acid, an aromatic carboxylic acid, a cyclic carboxylic acid, and a derivative of the foregoing.

The carboxylic acid can be an aliphatic carboxylic acid wherein the carboxylic acid is a monobasic or polybasic carboxylic acid. Examples of preferred monobasic carboxylic acids are members of the group consisting of acrylic acid, methacrylic acid, aconitic acid, itaconic acid, crotonic acid, acetic acid, lactic acid, gluconic acid, glucuronic acid, glycolic acid, and a derivative thereof. Suitable polybasic carboxylic acids are members of the group consisting of oxalic acid, malonic acid, succinic acid, glutaric acid, adipic acid, pimelic acid, maleic acid, fumaric acid, malic acid, tartartic acid, citric acid, a derivative thereof.

The carboxylic acid can be a hydroxycarboxylic acid. A preferred hydroxycarboxylic acid is a member of the group consisting of lactic acid, gluconic acid, glucuronic acid, glycolic acid and a derivative thereof.

The aliphatic carboxylic acid can also be a fatty acid as long as the co-polymer remains substantially water-soluble. A preferred fatty acid is a member of the group consisting of lauric acid, myristic acid, palmitic acid, stearic acid, arachidic acid, oleic acid, linoleic acid, linolenic acid, eleostearic acid, arachidonic acid and a derivative thereof.

The carboxylic acid can be an aromatic polybasic acid selected from the group consisting of phthalic acid, isophthalic acid and a derivative thereof.

Polymeric amino acids suitable for use in the present invention can be made, inter alia, by thermal condensation methods. See, for example, U.S. Pat. No. 5,057,597 to Koskan; U.S. Pat. No. 5,221,733 to Koskan et al.; U.S. Pat. No. 5,219,952 to Koskan et al.; Little et al., *American Chemical Society*, 97, 263–279 (1991) and U.S. Pat. No. 4,696,981 to Harada et al. The preparation of aspartic acid co-polymers has been described in U.S. Pat. No. 5,478,919 to Koskan et al.

The starting materials for the polymerization, i.e., the respective amino acid. monomers, can exist as optical isomers and can be polymerized either as a racemic mixture or as segregated optical isomers.

Counterions for the acidic amino acid salts, i.e., for the polyaspartates and polyglutamates include, but are not limited to, the alkali metal cations, preferably $Na^+$, $K^+$, and $Li^+$; alkali earth metal cations, preferably $Mg^{++}$, $Ca^{++}$ and $Ba^{++}$; transitional metal cations, preferably $Zn^{++}$, $Co^{++}$, $Fe^{++}$ and $Fe^{+++}$; and $NH_4^+$.

Particularly well-suited for the practice of the present invention are a co-polymer of aspartic acid and sulfoisophthalic acid in which the mole percent of aspartic acid is about 90% and that of sulfoisophthalic acid is about 10%, the co-polymer having a molecular size of about 2,565 Daltons; a co-polymer of aspartic acid and adipic acid in which the mole percent of aspartic acid is about 90% and that of adipic acid is about 10%, the co-polymer having a molecular size of about 7,640 Daltons; a co-polymer of aspartic acid and citric acid in which the mole percent of aspartic acid is about 80% and that of citric acid is about 20%, the co-polymer having a molecular size of about 1,653 Daltons.

The aforesaid co-polymeric acids increase the efficiency of fertilizers and the utilization of nutrients, both natural and synthetic. The nutrients can be those found naturally in the soil and plant growth medium or can be those which are added to the medium or can be those that are residual nutrients from previous nutrient treatments. More efficient utilization by the growing plants of both macronutrients, such as but not limited to, nitrogen (N), phosphorus (P), potassium (K) and micronutrients, such as but not limited to, calcium (Ca), magnesium (Mg), sulfur (S), zinc (Zn), iron (Fe), manganese (Mn), boron (B), cobalt (Co), molybdenum (Mo), copper (Cu) and nickel (Ni) is accomplished by employing the co-polymeric acids of this invention.

There are many uses and applications for the present invention in its various aspects. Illustrative are uses in agriculture, gardening, horticulture, hydroponics, forestry, land reclamation (e.g., landfills, soils with relatively high salt concentrations, etc.), and the like.

Suitable dosage rates of co-polymeric acids of the present invention, so as to provide a sufficient productivity enhancing amount of the co-polymeric acid to the plant to enhance nutrient utilization by the plant can be about 2 to about 500 ounces of the co-polymeric acid per acre. Crops with an abundance of foliage, such as wood crops, grain crops, cotton, etc., usually are treated at dosage rates in an intermediate range, i.e., about 25 to about 250 ounces per acre. Relatively lower dosage rates within the foregoing overall range, i.e., about 2 to about 25 ounces per acre, usually are sufficient for agricultural row crops, flowering nursery crops, and the like.

The co-polymeric acid can be made available to the plant as a separate treatment, or the co-polymer can be supplied to the plant together with a plant nutrient or a combination of plant nutrients. Solid as well as liquid dosage forms can be utilized for this purpose, e.g., aqueous solutions as well as solid forms containing conditioning substances such as particulate clays, depending upon the desired mode of application.

The present invention is further illustrated by the following examples which demonstrate more efficient utilization of plant growth nutrients by employing polyaspartic acid (PA) and co-polymeric acids thereof.

EXAMPLE 1

More Efficient Usage of Nutrients in Corn Plants

White corn (Early Sunglow; George W. Park Seed Co., Greenwood, S.C.) was grown in a greenhouse in one gallon pots filled with Fafard 3B potting soil. To each pot was added Peters™ 20-20-20 fertilizer in an amount representing a full dose of nutrients or a ⅓ dose of nutrients. A portion of the pots so treated also received an aqueous solution of polyaspartic acid (PA) (50 ml; 10 ppm by weight of PA having a weight average molecular weight (Mw) of about 3,000–5,000. The growth rates of the white corn plants in these pots were monitored, and representative plants were photographed 40 days after planting. These photographs are depicted in FIGS. 1 through 4.

Figure 3:
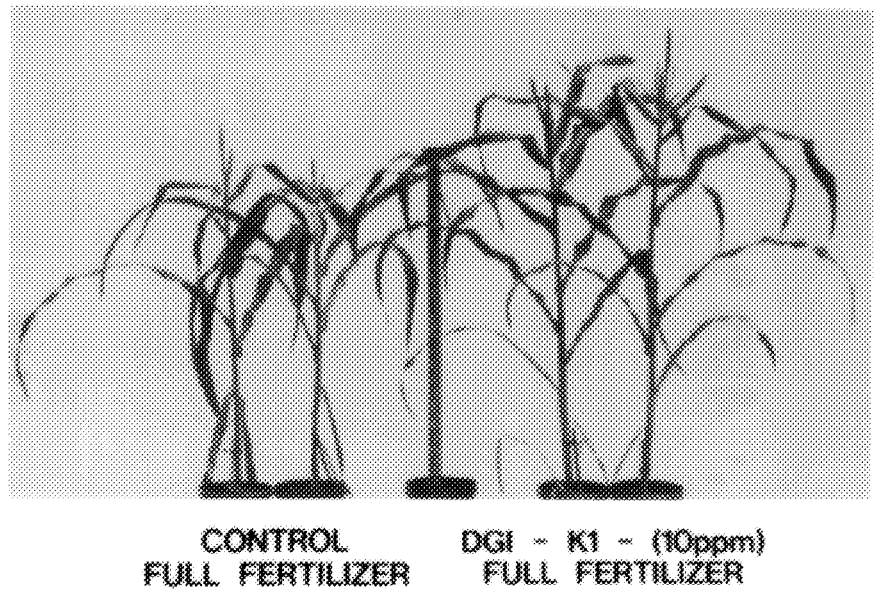
FIG. 3 shows corn plants 40 days after planting, both treated with the recommended fertilizer dosage and one plant also with 10 parts per million by weight of polyaspartic acid.
Figure 4:
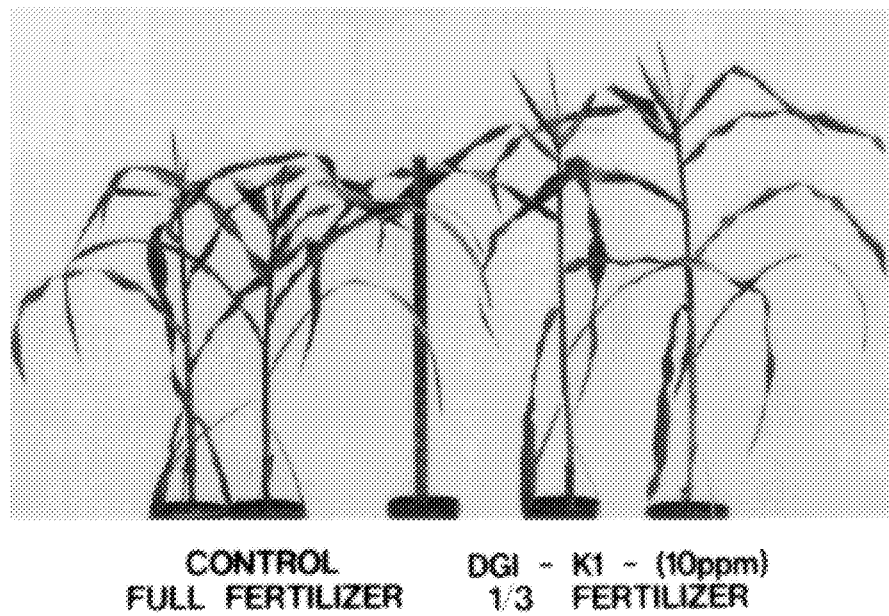
FIG. 4 shows corn plants 40 days after planting, one treated with the recommended fertilizer dosage and the other with one-third of the recommended fertilizer dosage but also with 10 parts per million by weight of polyaspartic acid.

These Figures show that the availability of PA to the plant enhanced plant growth at a reduced nutrient level, i.e., corn plants treated at one-third of the nutrient level but with 10 ppm of PA added (FIG. 4) show greater growth than corn plants will the full amount of nutrient. Corn plants grown using the full nutrient level also undergo enhanced growth when 10 ppm of polyaspartic acid is used along with the nutrient (FIG. 3). Both tests demonstrate a more efficient utilization of nutrients for plant growth.

EXAMPLE 2

Effects of Polyaspartic Acid on Growth Patterns of Corn Plants With No Added Fertilizer White corn (Early Sunglow; George W. Park Seed Co., Greenwood, S.C.) was grown in a greenhouse in one gallon pots filled with Fafard 3B potting soil. No fertilizer was added to any pot. A portion of the pots so treated received aqueous solutions of polyaspartic acid (PA) of varying dosage levels (50 ml of solution; 1 ppm, 10 ppm, 100 ppm, and 1,000 ppm of PA having a Mw of about 3,000–5,000. The growth rates of the white corn plants in these pots were monitored on a weekly basis and the data is shown in Table I, below.

TABLE I

GROWTH PATTERNS OF EARLY SUNGLOW CORN; NO ADDED FERTILIZER; SINGLE TREATMENT

| Dosages of PA | Height Change (inches) | | | |
| --- | --- | --- | --- | --- |
| | Week 1 | Week 2 | Week 3 | Week 4 |
| Control (No PA) | 13.0 | 9.0 | 6.4 | 5.2 |
| 1 ppm | 12.5 | 9.4 | 5.4 | 5.7 |
| 10 ppm | 11.6 | 11.0 | 5.0 | 7.0 |
| 100 ppm | 11.4 | 10.4 | 6.4 | 7.2 |
| 1000 ppm | 10.4 | 10.4 | 5.6 | 7.8 |

The data shown in Table I indicates that after one week of growth, corn plants with no added fertilizers but with PA added in dosages of 1 to 1,000 ppm received no benefit from PA treatment. After week 2 of corn plant growth, a beneficial effect was shown at all four dosage levels of PA. After three weeks of growth, only the 100 ppm dosage level of PA showed a benefit over no PA treatment. Finally after four weeks of corn plant growth, a low level of plant growth was occurring but increased growth rate was observed with all four dosage levels of PA. In summary, during the initial stage (first week) of corn plant growth PA did not increase growth rate without added fertilizer. However, after the next three weeks of growth of the plant, PA treatment was beneficial to plant productivity, based on growth, even without added fertilizer. These results indicate that more efficient utilization of existing nutrients in the soil has occurred.

EXAMPLE 3

Effects of Polyaspartic Acid on Potassium Uptake in Early Sunglow Corn With No Added Fertilizer White corn (Early Sunglow; George W. Park Seed Co., Greenwood, S.C.) was grown in a greenhouse in one gallon pots filled with Fafard 3B potting soil. No fertilizer or potassium source were added to the pots. The pots were treated with varying dosages of polyaspartic acid (PA) of about 3,000–5,000 Mw, as in Example 2. After a 40 day growing period, the plants were harvested and potassium content of the plants was determined.

TABLE II

EFFECT OF POLYASPARTIC ACID ON POTASSIUM UPTAKE; EARLY SUNGLOW CORN; NO ADDED FERTILIZER; SINGLE TREATMENT/SOIL

| Dosage of Polyaspartic Acid Used | % Potassium In Corn Plants | % Increase of Potassium In Corn Plants |
| --- | --- | --- |
| 0 ppm | 2.6 | — |
| 1 ppm | 2.7 | 3.8 |
| 10 ppm | 3.0 | 15.4 |
| 100 ppm | 2.8 | 7.7 |
| 1000 ppm | 3.2 | 23.1 |

The data reported in Table II shows that a more efficient uptake of potassium by the corn plants resulted when PA was used without added fertilizer. At the 1,000 ppm dosage level, a 23.1% increase in potassium content was found in the corn plants.

EXAMPLE 4

Effect of Polyaspartic Acid on Phosphorous Uptake in Early Sunglow Corn With No Added Fertilizer White corn (Early Sunglow; George W. Park Seed Co., Greenwood, S.C.) was grown in a greenhouse in one gallon pots filled with Fafard 3B potting soil as in Examples 2 and 3. No fertilizer or phosphorus-containing compounds were added to the pots. The pots were treated with varying dosages of polyaspartic acid (PA) (Mw 3,000–5,000) as in Examples 2 and 3. After a 40-day growing period, the plants were harvested and phosphorus content of the plants was determined. Results from this study are shown in Table III, below.

TABLE III

EFFECT OF POLYASPARTIC ACID ON PHOSPHORUS UPTAKE; EARLY SUNGLOW CORN; NO ADDED FERTILIZER; SINGLE TREATMENT/SOIL

| Dosage of Polyaspartic Acid Used | % Phosphorus In Corn Plants | % Increase of Phosphorus In Corn Plants |
|---|---|---|
| 0 ppm | 0.3 | — |
| 1 ppm | 0.36 | 20.0 |
| 10 ppm | 0.34 | 13.3 |
| 100 ppm | 0.38 | 26.7 |
| 1000 ppm | 0.44 | 46.7 |

The results listed in Table III show that use of PA at indicated dosage levels increased phosphorus uptake by corn plants when no fertilizer was added. This shows that a more efficient utilization of phosphorus sources existing in the soil has occurred. At the highest dosage level of PA, a 46.7% increase in phosphorus uptake by the corn plants was observed.

EXAMPLE 5

Effect of Polyaspartic Acid on Zinc Uptake in Early Sunglow Corn With No Added Fertilizer White corn (Early Sunglow) as was used in Examples 2, 3 and 4 was grown as before without added fertilizer. Again the same dosages of polyaspartic acid (PA) treatment for the corn plants was used as in Examples 2, 3 and 4. After a 40-day growing period, the plants were harvested and zinc content of the plants was determined. Results from this study are listed in Table IV, below.

TABLE IV

EFFECT OF POLYASPARTIC ACID ON ZINC UPTAKE; EARLY SUNGLOW CORN; NO ADDED FERTILIZER; SINGLE TREATMENT/SOIL

| Dosage of Polyaspartic Acid Used | Zinc In Corn Plants, ppm | % Increase of Zinc In Corn Plants |
|---|---|---|
| 0 ppm | 29 | — |
| 1 ppm | 48 | 65.5 |
| 10 ppm | 45 | 55.2 |
| 100 ppm | 54 | 86.2 |
| 1000 ppm | 79 | 172 |

The above results from Table IV indicate that PA effectively increased the uptake of zinc in corn plants with no use of additional fertilizer. Even at a low dosage level of 1 ppm PA, a 65% increase in zinc uptake was observed. At a dosage of 1000 ppm of PA, a 172% increase in zinc uptake was found, further demonstrating the ability of PA to efficiently increase utilization of zinc in plant soil.

EXAMPLE 6

Effect of Polyaspartic Acid to Increase Plant Utilization of Limited Amounts of Nutrients Duckweed (*Lemna Minor L.*) was grown in tap water containing as nutrient media a solution of Peters™ 20-20-20 fertilizer[1] (3 g/1.2 L) and a ¼-strength solution (750 mg/1.2 L) with and without 50 ppm by weight polyaspartic acid (PA). The nutrient media were adjusted to pH value of about 6.0. The Mw of the PA was about 3,000–5,000 (about 22 to about 40 repeating units).

[1] Total Nitrogen (N) . . . 20%
3.90% Ammoniacal Nitrogen
6.15% Nitrate Nitrogen
9.95% Urea Nitrogen Available Phosphoric Acid ($P_2O_5$) . . . 20% Soluble Potash ($K_2O$) . . . 20% Derived from: Ammonium, Phosphate, Potassium Nitrate, Urea. Commercially available from Grace-Sierra Horticultural Products Company, 1001 Yosemite Drive, Milpitas, Calif. 95035.

A single duckweed plant at the three-frond stage was placed in each flask. The flasks were then incubated under continuous light (500 lux) at 28°±2° C. for 21 days.

After 21 days, the plants were harvested, oven-dried, and weighed. Results show that nutrient reduction by 75% reduced plant weight by 74%, and that (a) no significant reduction in plant growth was found when PA was present in the medium with 25% nutrients indicating a more efficient use of a limited amount of nutrients and (b) plant growth was enhanced when PA was present in the medium with 100% nutrients. The results are presented in Table V, below. All reported values represent averages from 3 to 5 replicates.

TABLE V

RESULTS

| | Plant dry wt.-milligrams (mg) | | | |
|---|---|---|---|---|
| Treatment | Expt. A | Expt. B | Average | % Change |
| 100% Nutrients | 16.5 | 17.7 | 16.6 | 0 |
| 100% Nutrients + PA | 21.3 | 22.2 | 21.7 | 31 |
| 25% Nutrients | 4.7 | 4.0 | 4.4 | −74 |
| 25% Nutrients + PA | 15.2 | 16.7 | 16.0 | 0 |

EXAMPLE 7

Effect of Polyaspartic Acid on Biomass

The procedure described in Example 6, above, was followed except that a chemically defined nutrient medium having the composition described in U.S. Pat. No. 4,813,997 to Kinnersley et al. (Nickell's medium with Fe present as $Fe^{2+}$ chelated with EDTA) was used. The plants were grown in five replicate flasks, harvested after 21 days, and the combined dry weight of the harvested plants was determined. The content of potassium and phosphorus in the plants and in the spent media was determined as well. The observed results are presented in Table VI, below.

TABLE VI

CHANGES IN BIOMASS

Amount of Mineral (μg) Control/With PA

| Treatment | Plant Biomass (mg) | Spent Media | Plants |
|---|---|---|---|
| 100% Nutrients/ | 94.4/90.9 | | |
| 100% Nutrients + | | | |
| 50 ppm PA | | | |
| Potassium (K) | | 11,610/11,740 | 1540/1530 |
| Phosphorus (P) | | 1170/1140 | 250/280 |
| 25% Nutrients/ | 67.3/89.3 | | |
| 25% Nutrients + | | | |
| 50 ppm PA | | | |
| Potassium (K) | | 2420/1170 | 990/1530 |
| Phosphorus (P) | | 334/322 | 125/173 |
| 12.5% Nutrients/ | 54.1/62.7 | | |
| 12.5% Nutrients + | | | |
| 50 ppm PA | | | |
| Potassium (K) | | 955/718 | 769/942 |
| Phosphorus (P) | | 190/192 | 89/111 |

The above results show that nutrient concentration reduced by 75% caused a 29% reduction in plant biomass (94.4–67.3) and a 36% reduction in the potassium content of plants (1540–990). However, in the same treatments containing polyaspartic acid the plant biomass was barely reduced (90.9–89.3), and the potassium content was unchanged. Analysis of the spent media showed much less potassium in the media containing PA. This data also indicates that the polymers had increased the uptake of potassium into plants.

The above results also show a remarkably good correlation between potassium content and plant-biomass as can be seen in Table VII, below.

TABLE VII

CORRELATION BETWEEN POTASSIUM CONTENT AND BIOMASS

| | Nutrients | | Nutrients + PA | |
|---|---|---|---|---|
| Nutrient Amount | Biomass (mg) | K (mg) | Biomass (mg) | K (mg) |
| 100% | 94.4 | 1.54 | 90.9 | 1.53 |
| 25% | 67.3 | 0.99 | 89.3 | 1.53 |
| 12.5% | 54.1 | 0.77 | 62.7 | 0.94 |

Potassium is the most important metal needed for plant growth, and is the principal metal component of most fertilizers. However, heretofore no agent was known able to simultaneously increase the growth and potassium content of plants.

EXAMPLE 8

Plant Content of Nutrients

The content of other nutrients in plants from the full strength and ¼-strength treatments described in Example 7, above, was determined. The observed results are set forth in Table VIII, below.

TABLE VIII

PLANT NUTRIENT CONTENT

Amount, micrograms (μg)

| Elements | 100% Nutrients | 25% Nutrients | 25% Nutrients + 50 ppm PA |
|---|---|---|---|
| Zn | 9.2 | 2.6 | 3.7 |
| Mg | 70 | 43 | 49 |
| Fe | 2.5 | 1.0 | 5.9 |
| Ca | 340 | 172 | 243 |
| Cu | 3.9 | 3.7 | 3.2 |
| Mn | 4.1 | 1.1 | 1.1 |
| Biomass, mg | 94.4 | 67.3 | 89.3 |

These results show that the content of most other minerals needed for plant growth was also greatly increased by the presence of PA. Particularly noteworthy is the substantial increase in the iron content at reduced nutrient level.

EXAMPLE 9

Effect of Polyaspartic Acid to Increase Plant Utilization of Limited Amounts of Nutrients Duckweed (*Lemna minor L.*) was grown in tap water under conditions described in Example 6, above, and containing as nutrient media a solution of Peters™ 20-20-20 fertilizer at full strength (100% nutrients), half strength (50% nutrients), and one-quarter strength (25% nutrients), with and without 50 ppm polyaspartic acid (PA) (Code DGI-KI) of about 3,000–5,000 Mw.

The plants were harvested, oven dried, and weighed after 21 days. The average plant dry weight is reported in Table IX, below. All reported values represent 12 to 20 replicates.

TABLE IX

RESULTS

| Treatment | Average Plant Dry Wt. milligrams (mg) |
|---|---|
| 100% Nutrients | 15.5 |
| 100% Nutrients + PA | 20.2 |
| 50% Nutrients | 8.8 |
| 50% Nutrients + PA | 15.1 |
| 25% Nutrients | 3.7 |
| 25% Nutrients + PA | 9.9 |

The foregoing results are depicted graphically in FIG. 5. These results show that the addition of PA permits decreasing the nutrient level by about 50% without a significant decrease in plant growth. From FIG. 5 it can also be seen that while the addition of PA to the nutrient solution increased plant growth at all nutrient levels, the effect of PA was much greater at the relatively lower levels of nutrients. Specifically, an increase in plant growth of about 168% was noted when PA was added to a 25% nutrient solution, and an increase of about 29% was noted when PA was added to a 200% nutrient solution. Therefore, when limited amounts of nutrients were available for plant growth, use of PA increased the efficiency of usage of these nutrients.

EXAMPLE 10

Effect of Polyaspartic Acid to Increase Bean Plant Utilization of Limited Amounts of Nutrients Garden beans (Mayo's Red Peanut Bush) were grown in the greenhouse in gallon pots filled with Fafard 3B potting soil. Ten pots were given 50 ml of a 7,500 ppm solution of Peters™ 20-20-20 nutrient. Twenty pots were given 50 ml of a 2,500 ppm Peters™ nutrient solution, and 10 of these pots were also given four weekly treatments of 50 ml aliquots of a 1 ppm solution of PA in water. When the bean plants flowered, they were taken outside for insect pollination. The beans that grew were harvested. The weight of beans on each plant was then determined. Results in Table X, below, show that PA increased reproductive growth results in a greater weight yield of beans from each plant. The increase in bean yield in the ⅓ fertilizer treatment with PA compared to the fertilizer alone, was statistically significant with Duncan's multiple range test.

TABLE X

YIELD OF BEANS

| Treatment | Average Fresh Weight of Beans/Plant, g |
|---|---|
| 100% Nutrients | 6.4 |
| 33% Nutrients | 3.9 |
| 33% nutrients + 1 ppm PA | 7.2 |

The foregoing data show that when one-third the regular nutrient level was used along with 1 ppm of PA, the average fresh weight of bean/plant increased by 85%. This was a greater yield than was obtained when the 100% nutrient level was used. Under the conditions of limited nutrient availability, use of PA increased the efficiency of nutrient utilization resulting in increased bean yields.

EXAMPLE 11

Effect of Polyaspartic Acid to Increase Rapeseed Plant Utilization of Limited Amounts of Nutrients A fast growing variety of rapeseed (*Brasica rapus*) was obtained from the Crucifer Genetics Cooperative at the University of Wisconsin. This variety was grown in 9-cm pots in a greenhouse. Pots were given 50 ml of a full strength solution of Peters™ 20-20-20 nutrient (7,500 ppm) in water, or the same volume of a 3,750 ppm solution in water. Some of the pots were given 50 ml of a 2 or 20 ppm solution of polyaspartic acid (PA) in water as a single treatment. Plants were pollinated by hand when they flowered. Mature seed pods were harvested. The observed results are reported in Table XI, below.

TABLE XI

RAPESEED HARVEST

| Treatment | Average # Pods per Plant | Average Dry Weight of Pods per Plant, mg |
|---|---|---|
| Full Nutrient | 3.8 | 202 |
| 50% Nutrient | 2.9 | 174 |
| 50% Nutrient + 2 ppm PA | 4.8 | 283 |
| 50% Nutrient + 20 ppm PA | 5.2 | 290 |
| Full Nutrient + 2 ppm PA | 5.0 | 271 |

The above results show that average grain yield was higher in plants given PA than in plants receiving nutrient alone. PA increased grain yield in plants given both full and ½ strength nutrient. In many plants yield was higher for plants given ½ strength nutrient +2 ppm PA than in plants receiving full fertilizer alone. This result shows that use of PA increased the efficiency of utilization of a limited amount of nutrients available to the rapeseed plants.

EXAMPLE 12

Effect of Polyaspartic Acid on Duckweed Plants Grown in Tap Water

Duckweed was grown in tap water and in tap water solutions of polyaspartic acid (PA) following the procedure described in Example 6, above. Table XII, below, presents the compositions of the aqueous growth medium and the observed corresponding results. In each growth medium containing nutrients, the nutrient was Peters™ 20-20-20, and in each solution containing PA, the concentration of PA was 50 ppm.

TABLE XII

EFFECT OF POLYASPARTIC ACID ON DUCKWEED PLANTS GROWN IN TAP WATER

| | Aqueous Growth Medium | Plant Dry Wt. (mg) | % Change |
|---|---|---|---|
| A. | Nutrient (2.2 g/L) | 37 | |
| | Nutrient (2.2 g/L) + PA | 78 | 111 |
| B. | Nutrient (1.1 g/L) | 18 | |
| | Nutrient (1.1 g/L) + PA | 57 | 217 |
| C. | Nutrient (0.55 g/L) | 17 | |
| | Nutrient (0.55 g/L) + PA | 22 | 72 |
| D. | Tap water only[1] | 20 | |
| | Tap water + PA | 26 | 30 |

[1]There is some mineral content in tap water.

In the above table, each treatment dosage of nutrient combined with PA is compared to the same nutrient dosage without PA (the control) and % change in plant weight compared to the corresponding control is given. The above results show that PA was least effective at promoting plant growth when it was given with treatment D that has no added nutrients. If, in fact, PA was acting as a fertilizer, it should have been most effective (as measured by relative % change over control) when plants had no added nutrient for growth. Actually, the reverse was observed to be true. PA was only effective in promoting plant growth in conjunction with a real nutrient source. In treatment D, when no nutrient was added, use of PA still permitted increased plant growth by facilitating uptake of minerals from the tap water.

EXAMPLE 13

Effect of Polyaspartic Acid on Duckweed Plants Grown in Deionized Water

Duckweed was grown in deionized water and in deionized water solution of polyaspartic acid (PA) following the procedure described in Example 6, above, except that the plants were harvested after four weeks instead of 21 days. Table XIII, below, presents the composition of the aqueous growth media that was used and the corresponding observed results. Because the biomass of each plant was so minimal, plants from eight replicate flasks of each treatment were combined to provide enough plant material to be weighed accurately.

TABLE XIII

EFFECT OF POLYASPARTIC ACID ON DUCKWEED PLANTS GROWN IN DEIONIZED WATER

| | Aqueous Growth Medium | Plant Dry Wt. (mg) | % Change |
|---|---|---|---|
| A. | Deionized water | 8 | |
| B. | Deionized water + PA (50 ppm) | 2 | −75 |

The above results show that PA did not increase plant growth when added to deionized water from which all minerals had been removed. This effect would not have been observed if PA was functioning as a fertilizer.

The tests performed with duckweed plants as described in Examples 12 and 13, above, demonstrate (a) that PA had minimal biological activity when supplied to plants grown in tap water and (b) that PA itself showed no nutrient or fertilizer activity with regard to these plants when the plants were grown in deionized water.

In U.S. Pat. No. 4,839,461 to Boehmke it is stated that K, Mg, and Ca salts of polyaspartic acid are suitable for use as fertilizers. No experimental evidence or examples are given to support this statement, however. The above tests with Duckweed plant in tap water and deionized water show that PA itself does not act as a fertilizer. It is likely that if the Ca, K and Mg salts of PA act as fertilizers, this activity is due to the nutrient value of Ca, K and Mg ions themselves rather than PA.

EXAMPLE 14

Effect of Polyaspartic Acid on Corn Plants

White corn (*Zea mays L.*) seed (5145 Truckers Favorite; George W. Park Seed Co., Greenwood, S.C.) was planted in 8-cm black round pots with Fafard 3B potting soil. Each pot was given 0.3g, 0.15g, or 0.075g of Peters™ 20-20-20 nutrient. Five pots representing each treatment were kept as controls, five pots were given 50 ml of 5 ppm aqueous polyaspartic acid (PA) solution, and five pots 50 ml of a 500 ppm aqueous PA solution. After six weeks the plants were harvested, and the fresh weight and nitrogen content of the harvested plants was determined. The observed results are reported in Table XIV, below.

TABLE XIV

EFFECT OF POLYASPARTIC ACID ON CORN PLANTS

| Treatment | Fresh wt., g | Average N Content, mg |
| --- | --- | --- |
| 100% Nutrients | 45.8 | 67.6 |
| 100% Nutrients + 5 ppm PA | 46.5 | 75.7 |
| 100% Nutrients + 500 ppm PA | 50.2 | 73.2 |
| 50% Nutrients | 34.7 | 40.5 |
| 50% Nutrients + 5 ppm PA | 45.6 | 57.6 |
| 50% Nutrients + 500 ppm PA | 38.6 | 49.6 |
| 25% Nutrients | 24.1 | 29.6 |
| 25% Nutrients + 5 ppm PA | 31.7 | 36.2 |
| 25% Nutrients + 500 ppm PA | 38.3 | 47.8 |

Above results show that PA enables plants to be grown with a 50% reduction in nutrients without showing any reduction in growth. Simultaneously with increasing the corn biomass, PA also increased the nitrogen content of the corn. Plants grown with 25% nutrients and 500 ppm PA contained more nitrogen than plants grown with 50% nutrients that were given twice the amount of nitrogen.

EXAMPLE 15

Environmental Stability of Polyaspartic Acid

A nutrient solution was made by adding Peters™ 20-20-20 nutrient (375 mg) to tap water (150 ml). The solution was divided into three aliquots. One 50-ml aliquot was maintained as a control. To another aliquot was added 1,000 ppm of polyaspartic acid, and 1000 ppm of lactic acid oligomer containing less than ten lactic acid residues and obtained by thermal condensation of 88% L-lactic acid by heating at 70° C. for 4 hours followed by heating under vacuum at 100° C. for 4 hours was added to the last 50-ml aliquot.

The turbidity of the samples were measured every day to ascertain the extent of microbial growth in each sample. Within a few days the solution containing the lactic acid oligomer had become milky, indicating microbial contamination. The sample containing polyaspartic acid remained substantially clear, even after 7 days. The observations are compiled in Table XV, below.

TABLE XV

TURBIDITY MEASUREMENTS

| | DAYS | | | | |
| --- | --- | --- | --- | --- | --- |
| | 1 | 2 | 3 | 4 | 5 |
| Control | 0 | 0 | 0 | 0 | 0 |
| Polyaspartic Acid | −0.04 | +0.25 | +0.26 | +0.40 | +0.95 |
| Lactic Acid Oligomer | −0.11 | +2.20 | +3.45 | +16.5 | +382.0 |

Results indicate that polyaspartic acid has a relatively longer life in the environment.

EXAMPLE 16

Nutrient Composition for Hydroponic Growing

An illustrative aqueous composition suitable for incorporating polyamino acid or a crosslinked polyamino acid embodying the present invention and well suited for hydroponic farming is set forth in Table XVI, below.

TABLE XVI

HYDROPONIC GROWING MEDIUM

| Nutrients | ppm by weight |
| --- | --- |
| Nitrogen as N | 50 |
| Phosphorus as P | 48 |
| Potassium as K | 210 |
| Magnesium as Mg | 30 |
| Sulfates as $SO_4^{-2}$ | 117 |
| Sodium as Na | 3.619 |
| Chlorides as Cl | 0.04 |
| Iron as Fe | 3 |
| Zinc as Zn | 0.15 |
| Copper as Cu | 0.15 |
| Boron as B | 0.5 |
| Manganese as Mn | 0.5 |
| Molybdenum as Mo | 0.1 |
| Water, q.s. | |

EXAMPLE 17

Stress Protection and Enhanced Plant Productivity by Co-polymeric Acids

Duckweed (*Lemna minor L.*) was grown in an aqueous solution containing relatively low levels of nutrients as shown in the following Table XVII.

TABLE XVII

LOW NUTRIENT COMPOSITION

| Nutrient Element | Concentration (ppm as element) |
| --- | --- |
| Nitrogen (N) | 12.5 |
| Phosphorus (P) | 3 |
| Potassium (K) | 12 |
| Calcium (Ca) | 10 |
| Magnesium (Mg) | 4 |

TABLE XVII-continued

LOW NUTRIENT COMPOSITION

| Nutrient Element | Concentration (ppm as element) |
|---|---|
| Sulfur (S) | 14 |
| Iron (Fe) | 1 |
| Water, q.s. | |

Tests were performed in which the plants were grown in separate flasks under controlled conditions employing the low nutrient solution which was enhanced by the addition of 50 ppm by weight of a selected co-polymeric acid, identified as Compound A, B or C in Table XVIII, below.

TABLE XVIII

CO-POLYMERIC ACID

| | |
|---|---|
| A. | aspartic acid (90 mole percent)-sulfoisophthalic acid (10 mole percent), sodium salt (Mw about 2,565 Daltons) |
| B. | aspartic acid (80 mole percent)-citric acid (20 mole percent), sodium salt (Mw about 1,653 Daltons) |
| C. | aspartic acid (90 mole percent)-adipic acid (10 mole percent), sodium salt (Mw about 7,640 Daltons) |

For evaluating stress protection, a similar series of tests were performed in which the plants were grown employing each of the foregoing compositions to which 3 ppm of $Cu^{++}$ ion was also added. For each test, the enhanced nutrient solution was adjusted to pH 6.7±0.1 and five replications were performed, both with and without the added copper.

A single duckweed plant at the three-frond stage was placed in each flask. Each flask was then incubated under continuous light in a greenhouse at a temperature of about 28°±2° C. for three days. The plants were then harvested, oven dried and weighed. The average dry weight of the plant is reported in Table XIX, below. All reported values represent an average of five replicates.

TABLE XIX

STRESS PROTECTION AND PLANT PRODUCTIVITY
AVERAGE BIOMASS (mg)

| Compound | no additional $Cu^{++}$ | 3 ppm $Cu^{++}$ |
|---|---|---|
| None (Control) | 9.648 | 3.338 |
| A | 11.314 | 5.270 |
| B | 10.828 | 5.040 |
| C | 12.766 | 4.916 |

The data show that the addition of each of the co-polymeric acids to each low level nutrient solution resulted in enhanced plant productivity based on an average biomass increase of more than 10%. The data also show that the stress producing effect of copper toxicity limited plant growth to 35% as compared to the plant growth at non-toxic copper levels. The presence of each co-polymeric acid afforded a degree of stress protection by enhancing plant productivity to 47% for Compounds A and B and 39% for Compound C as compared to only 35% for the control.

The foregoing specification and the Examples are intended to illustrate the present invention, but are not to be taken as limiting.

We claim:

1. A method for enhancing plant productivity which comprises supplying to a plant a productivity enhancing amount of a water-soluble co-polymer of a carboxylic acid and an amino acid having an acidic alkyl group, —RCOOH, in which R contains 1 to about 22 carbon atoms, wherein the amino acid residue constitutes at least about 20 mole percent of the co-polymer, the co-polymer having a molecular size larger than about 1,600 Daltons.

2. The method of claim 1 wherein the amino acid is aspartic acid.

3. The method of claim 1 wherein the amino acid is glutamic acid.

4. The method of claim 1 wherein the molecular size of the co-polymer is about 2,000 to about 100,000 Daltons.

5. The method of claim 1 wherein plant nutrients are supplied to the plant together with the co-polymer.

6. The method of claim 1 wherein the productivity enhancing amount of the co-polymer is supplied to the plant as a solid and at a level of about 2 to about 500 ounces per acre.

7. The method of claim 1 wherein the productivity enhancing amount of the co-polymer is supplied to the plant as an aqueous solution containing at least about 10 parts per billion of the co-polymer.

8. The method of claim 1 wherein the productivity enhancing amount of the co-polymer is supplied to the plant as an aqueous solution containing about 0.1 to about 1,000 parts per million of the co-polymer.

9. The method of claim 1 wherein the carboxylic acid is selected from the group consisting of an aliphatic acid, an aromatic acid, a cyclic acid and a derivative thereof.

10. The method of claim 1 wherein the carboxylic acid is an aliphatic carboxylic acid.

11. The method of claim 10 wherein the aliphatic carboxylic acid is a monobasic carboxylic acid selected from the group consisting of acrylic acid, methacrylic acid, aconitic acid, itaconic acid, 2-acrylamido-2-methylpropanesulfonic acid, crotonic acid, lactic acid, gluconic acid, acetic acid, glucuronic acid, glycolic acid and a derivative thereof.

12. The method of claim 10 wherein the aliphatic carboxylic acid is a polybasic carboxylic acid selected from the group consisting of oxalic acid, malonic acid, succinic acid, glutaric acid, adipic acid, pimelic acid, maleic acid, fumaric acid, malic acid, tartaric acid, citric acid, and a derivative thereof.

13. The method of claim 10 wherein the aliphatic carboxylic acid is a fatty acid selected from the group consisting of lauric acid, myristic acid, palmitic acid, stearic acid, arachidic acid, oleic acid, linoleic acid, linolenic acid, eleostearic acid, arachidonic acid and a derivative thereof.

14. The method of claim 1 wherein the carboxylic acid is an aromatic polybasic acid selected from the group consisting of phthalic acid, isophthalic acid, terephthalic acid and a derivative thereof.

15. A method for enhancing plant productivity which comprises supplying to a plant a productivity enhancing amount of a water-soluble co-polymer of a poly(carboxylic acid) and a poly(amino acid) having an acidic alkyl group, -RCOOH, in which R contains 1 to about 22 carbon atoms, wherein the poly(amino acid) constitutes at least about 20 mole percent of the co-polymer, the co-polymer having a molecular size larger than about 1,600 Daltons.

16. The method of claim 15 wherein the poly(amino acid) is poly(aspartic acid).

17. The method of claim 15 wherein the poly(amino acid) is poly(glutamic acid).

18. The method of claim 15 wherein the molecular size of the co-polymer is about 2,000 to about 100,000 Daltons.

19. The method of claim 15 wherein plant nutrients are supplied to the plant together with the co-polymer.

20. The method of claim 15 wherein the productivity enhancing amount of the co-polymer is supplied to the plant as a solid at a level of about 2 to about 500 ounces per acre.

21. The method of claim 15 wherein the productivity enhancing amount of the co-polymer is supplied to the plant as an aqueous solution containing at least about 10 parts per billion of the co-polymer.

22. The method of claim 15 wherein the productivity enhancing amount of the co-polymer is supplied to the plant as an aqueous solution containing about 0.1 to about 1,000 parts per million of the co-polymer.

23. The method of claim 15 wherein the poly(carboxylic acid) is selected from the group consisting of an aliphatic acid, an aromatic acid, a cyclic acid, and a derivative thereof.

24. The method of claim 15 wherein the poly(carboxylic acid) is an aliphatic carboxylic acid.

25. The method of claim 15 wherein the poly(carboxylic) is a aliphatic monobasic carboxylic acid selected from the group consisting of acrylic acid, methacrylic acid, aconitic acid, itaconic acid, 2-acrylamido-2-methylpropanesulfonic acid, crotonic acid, lactic acid, gluconic acid, glucuronic acid, acetic acid, glycolic acid and a derivative thereof.

26. The method of claim 15 wherein the poly(carboxylic acid) is an aliphatic polybasic carboxylic acid selected from the group consisting of oxalic acid, malonic acid, succinic acid, glutaric acid, adipic acid, pimelic acid, maleic acid, fumaric acid, malic acid, tartaric acid, citric acid, and a derivative thereof.

27. The method of claim 15 wherein the poly(carboxylic acid) is an aromatic polybasic acid selected from the group consisting of phthalic acid, isophthalic acid, terephthalic acid and derivatives thereof.

28. The method of claim 1 wherein the amino acid) is aspartic acid and the carboxylic acid is sulfoisophthalic acid, the mole percent of the amino acid is about 90% and the mole of the carboxylic acid is about 10%, the molecular size of the co-polymer is about 2,565 Daltons.

29. The method of claim 1 wherein the amino acid is aspartic acid and the carboxylic acid is adipic acid, the mole percent of the amino acid is about 90% and the mole ratio of the carboxylic acid is about 10%, the molecular size of the co-polymer is about 7,640 Daltons.

30. The method of claim 1 wherein the amino acid is aspartic acid and the carboxylic acid is citric acid, the mole percent of the amino acid is about 80% and the mole ratio of the carboxylic acid is about 20%, the molecular size of the co-polymer is about 1,653 Daltons.

31. The method of claim 1 wherein the carboxylic acid is a hydroxycarboxylic acid selected from the group consisting of lactic acid, gluconic acid, glucuronic acid, glycolic acid and a derivative thereof.

32. The method of claim 1 wherein the co-polymer is in the form of a salt having a substantially non-toxic counterion selected from the group consisting of an alkali metal, an alkali earth metal, a transition metal, and ammonium.

* * * * *